(12) United States Patent
Yuzawa

(10) Patent No.: US 9,638,713 B2
(45) Date of Patent: May 2, 2017

(54) NON-TRANSITORY COMPUTER READABLE MEDIUM, ACTION DETECTION APPARATUS, AND ACTION DETECTION METHOD

(71) Applicant: FUJI XEROX CO., LTD., Tokyo (JP)

(72) Inventor: Hideto Yuzawa, Kanagawa (JP)

(73) Assignee: FUJI XEROX CO., LTD., Tokyo (JP)

(*) Notice: Subject to any disclaimer, the term of this patent is extended or adjusted under 35 U.S.C. 154(b) by 798 days.

(21) Appl. No.: 13/768,628

(22) Filed: Feb. 15, 2013

(65) Prior Publication Data

US 2014/0039827 A1 Feb. 6, 2014

(30) Foreign Application Priority Data

Aug. 6, 2012 (JP) .................. 2012-174069

(51) Int. Cl.
  *G01P 15/00* (2006.01)
  *G01P 15/18* (2013.01)
  *G01P 15/08* (2006.01)
  *G01P 13/00* (2006.01)

(52) U.S. Cl.
  CPC .............. *G01P 15/18* (2013.01); *G01P 13/00* (2013.01); *G01P 15/00* (2013.01); *G01P 15/0891* (2013.01); *A61B 2562/0219* (2013.01)

(58) Field of Classification Search
  CPC .................. G01P 15/18; G01P 15/0891; A61B 2562/0219
  USPC ......................................................... 702/141
  See application file for complete search history.

(56) References Cited

U.S. PATENT DOCUMENTS

| 6,677,969 | B1 | 1/2004 | Hongo | |
| 7,753,861 | B1* | 7/2010 | Kahn | A61B 5/1118 482/8 |
| 2003/0191582 | A1* | 10/2003 | Terada | G01C 21/16 701/500 |
| 2009/0088204 | A1* | 4/2009 | Culbert | G06F 3/017 455/556.1 |

(Continued)

FOREIGN PATENT DOCUMENTS

| JP | A-10-198476 | 7/1998 |
| JP | A-2000-163196 | 6/2000 |

*Primary Examiner* — Manuel L Barbee
*Assistant Examiner* — Jeremy Bishop
(74) *Attorney, Agent, or Firm* — Oliff PLC

(57) ABSTRACT

A non-transitory computer readable medium stores a program causing a computer to execute a process. The process includes calculating a variance of acceleration in individual sections obtained by dividing, by a first predetermined time interval, acceleration information for multiple axis directions detected from a subject whose action is to be determined; extracting, as a first candidate region, a section with the largest variance of acceleration from among the sections; calculating a variance of acceleration in individual sections obtained by shifting the first candidate region forward and backward by a second predetermined time interval; selecting, as a second candidate region, a section with the largest variance of acceleration from among the first candidate region and the sections obtained by shifting the first candidate region forward and backward; calculating a feature value for the second candidate region; and determining the action of the subject based on the feature value.

6 Claims, 15 Drawing Sheets

(56) References Cited

U.S. PATENT DOCUMENTS

2012/0004881 A1* 1/2012 Jung .................... G01C 22/006
　　　　　　　　　　　　　　　　　　　　　　702/141
2012/0259578 A1* 10/2012 Bevilacqua ........... G06F 1/1694
　　　　　　　　　　　　　　　　　　　　　　702/141
2012/0303271 A1* 11/2012 Chowdhary ......... A61B 5/0022
　　　　　　　　　　　　　　　　　　　　　　701/433

* cited by examiner

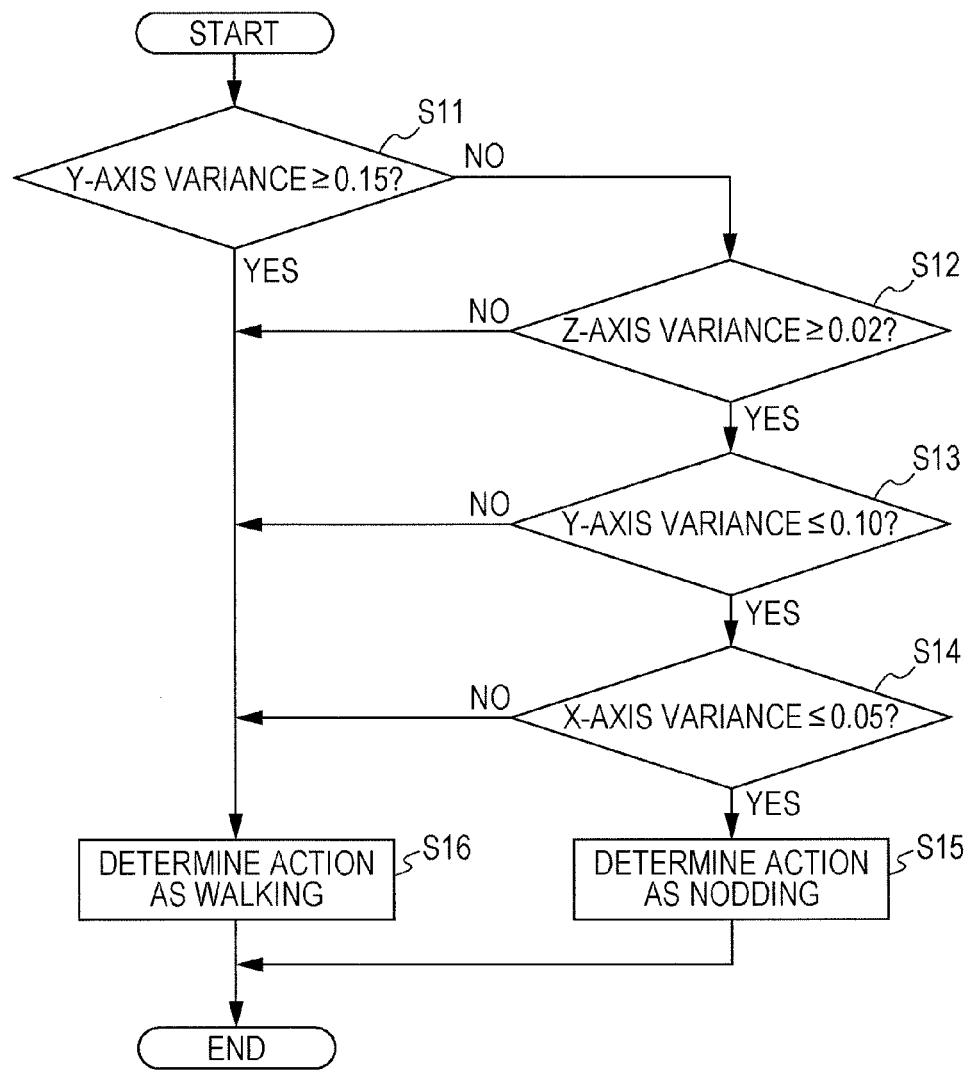

NON-TRANSITORY COMPUTER READABLE MEDIUM, ACTION DETECTION APPARATUS, AND ACTION DETECTION METHOD

CROSS-REFERENCE TO RELATED APPLICATIONS

This application is based on and claims priority under 35 USC 119 from Japanese Patent Application No. 2012-174069 filed Aug. 6, 2012.

BACKGROUND

Technical Field

The present invention relates to a non-transitory computer readable medium, an action detection apparatus, and an action detection method.

Summary

According to an aspect of the invention, there is provided a non-transitory computer readable medium storing a program causing a computer to execute a process for detecting an action. The process includes calculating a variance of acceleration in individual sections obtained by dividing pieces of acceleration information for multiple axis directions by a first predetermined time interval, the pieces of acceleration information being detected from a subject whose action involving a movement is to be determined; extracting, as a first candidate region, a section with the largest variance of acceleration from among the sections; calculating a variance of acceleration in individual sections obtained by shifting the first candidate region forward and backward by a second predetermined time interval; selecting, as a second candidate region, a section with the largest variance of acceleration from among the first candidate region, the section obtained by shifting the first candidate region forward, and the section obtained by shifting the first candidate region backward; calculating a feature value for the selected second candidate region; and determining the action of the subject on the basis of the calculated feature value.

BRIEF DESCRIPTION OF THE DRAWINGS

Exemplary embodiments of the present invention will be described in detail based on the following figures, wherein:

FIG. 4A is a graph illustrating an example of values of acceleration information in individual axis directions, whereas

FIG. 5A is a graph illustrating another example of values of acceleration information in the individual axis directions, whereas

FIG. 6A is a graph illustrating an example of values of acceleration information in the individual axis directions and a candidate region, whereas

FIG. 7A is a graph illustrating another example of values of acceleration information in the individual axis directions and a candidate region, whereas

FIG. 8 is a flowchart illustrating an example operation performed by a nodding determining unit;

FIG. 10A is a graph illustrating an example of a value of acceleration information in the Z axis direction, whereas

FIG. 11A is a graph illustrating another example of a value of acceleration information in the Z axis direction, whereas

FIG. 12A is a graph illustrating an example of values of acceleration information in the individual axis directions, whereas

FIG. 13A is a graph illustrating another example of values of acceleration information in the individual axis directions, whereas

FIG. 14A is a graph illustrating an example of values of acceleration information in the individual axis directions and a candidate region, whereas FIG. 15A is a graph illustrating another example of values of acceleration information in the individual axis directions and a candidate region, whereas

DETAILED DESCRIPTION

Configuration of Sensor

Figure 1A:
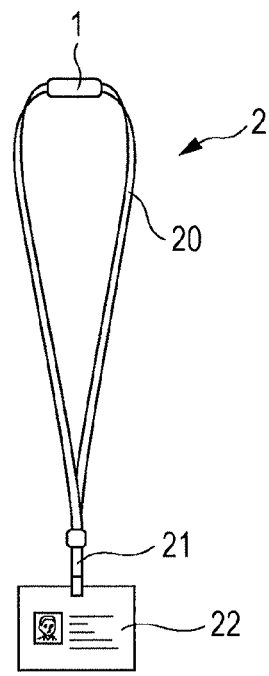
FIGS. 1A and 1B are schematic diagrams illustrating an example configuration of a sensor used by an action detection apparatus according to an exemplary embodiment of the present invention.
Figure 1B:
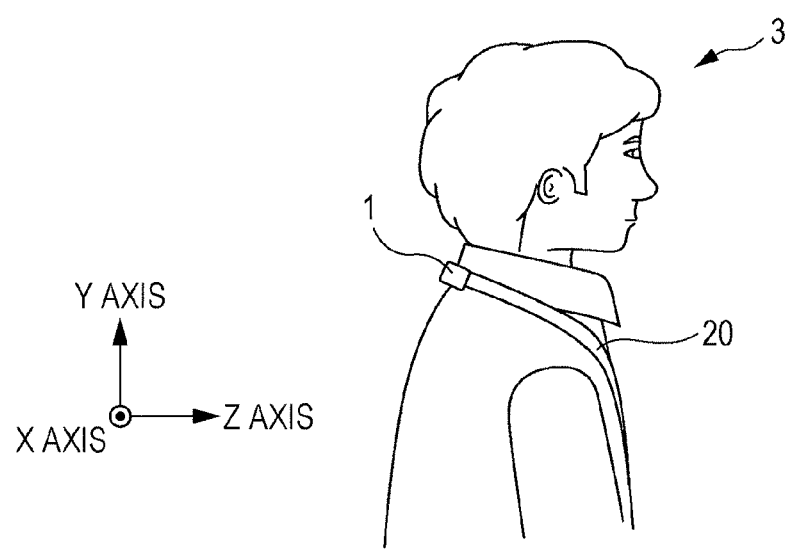

FIGS. 1A and 1B are schematic diagrams illustrating an example configuration of a sensor used by an action detection apparatus according to an exemplary embodiment of the present invention.

As illustrated in FIG. 1A, a sensor 1 is attached to a strap portion 20 of a neck strap 2, which generally has an integrated circuit (IC) card holder 22 that contains an IC card or the like therein. The strap portion 20 and the IC card holder 22 are connected to each other via a clip portion 21.

As illustrated in FIG. 1B, when a user 3 wears the neck strap 2, the sensor 1 is arranged to be in contact with a back portion of the neck of the user 3 because of the weight of the IC card holder 22 and moves in accordance with the movement of the user 3. It is assumed hereinafter that the Z-axis direction indicates the front side of the user 3, the Y-axis direction indicates the upper side of the user 3, and the X-axis direction indicates the right side of the user 3 in the coordinate system of the sensor 1 as illustrated in FIG. 1B.

In addition to being attached to the neck strap 2, the sensor 1 may be directly attached to the head of the user 3 or may be held in a breast pocket of the shirt worn by the user 3.

Configuration of Action Detection Apparatus

Figure 2:
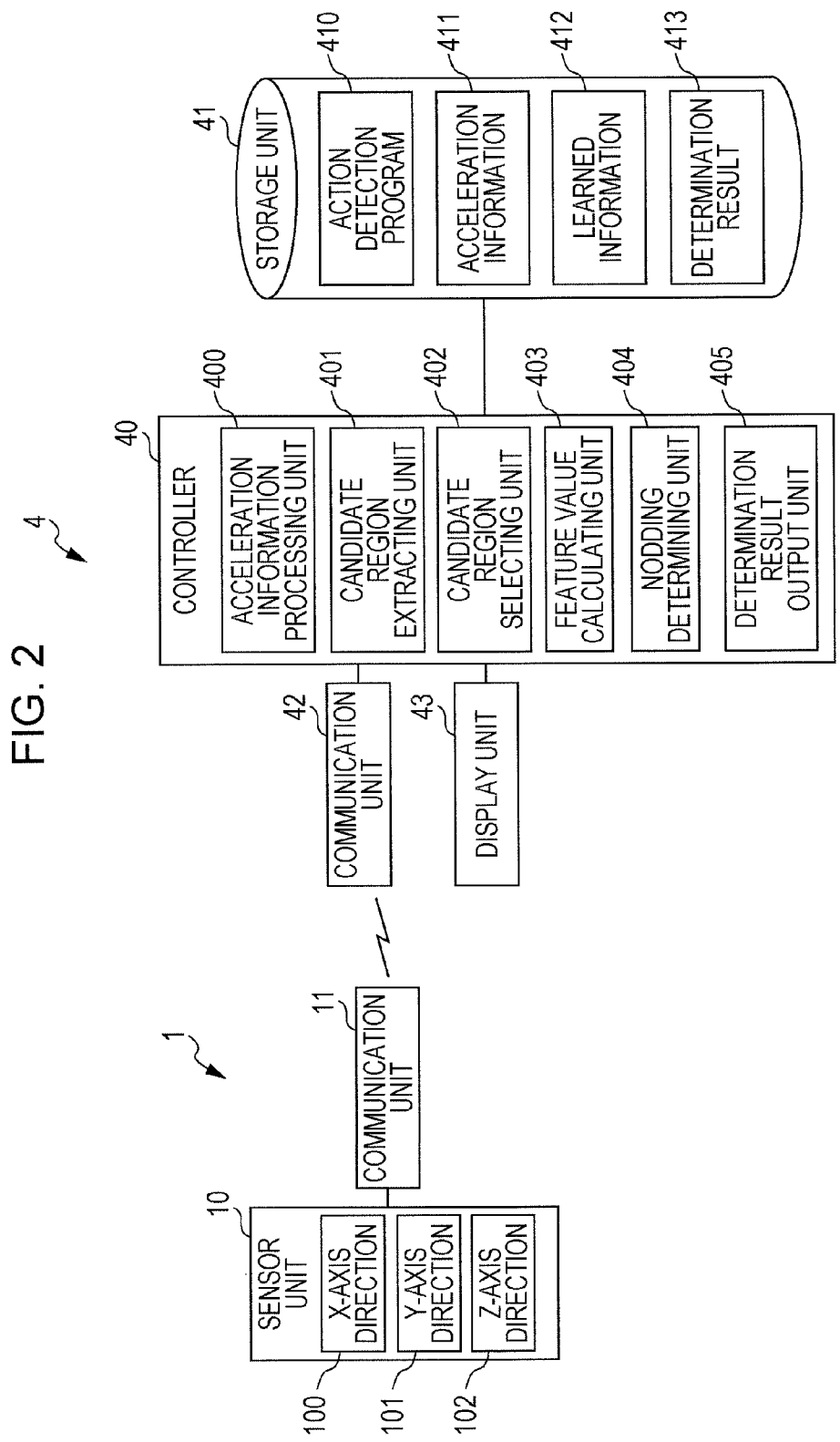
FIG. 2 is a schematic block diagram illustrating an example configuration of the action detection apparatus.

FIG. 2 is a schematic block diagram illustrating an example configuration of the action detection apparatus.

This action detection apparatus 4 detects, as an example of quantities representing a movement of the user 3, accelerations in multiple axis directions by using the sensor 1. The action detection apparatus 4 then detects an action of the user 3 based on feature values calculated from the accelerations in the multiple axis directions. The following describes an example case in which a movement involving the neck of the user 3, e.g., nodding, is detected as an example of the action. Here, other movements involving the neck, such as shaking the head to express a denial and tilting the head on one side to express a doubt, may be detected. Alternatively, the position of the sensor 1 may be modified and movements involving parts other than the neck, for example, movements involving a hand, an arm, a leg, etc. may be detected.

The action detection apparatus 4 includes a controller 40, a storage unit 41, a communication unit 42, and a display unit 43, such as a liquid crystal display (LCD). The controller 40 includes a central processing unit (CPU), controls individual components, and executes various programs. The storage unit 41 includes a hard disk drive (HDD) or a storage medium, such as a flash memory, and stores information. The communication unit 42 communicates, wirelessly or with a cable, with a communication unit 11 of the sensor 1 that detects accelerations in multiple axis directions relative to the user 3.

In addition to acceleration sensors that detect accelerations, a sensor unit 10 may use gyro sensors, geomagnetic sensors, or vibration sensors to detect other quantities regarding a movement of the user 3.

The action detection apparatus 4 may be, for example, a personal computer (PC), a personal digital assistant (PDA), or a mobile phone.

The controller 40 executes an action detection program 410, which will be described later, thereby functioning as an acceleration information processing unit 400, a candidate region extracting unit 401, a candidate region selecting unit 402, a feature value calculating unit 403, a nodding determining unit 404, and a determination result output unit 405.

The acceleration information processing unit 400 receives, as acceleration information, accelerations detected by the sensor 1; performs processing, such as normalization and direction determination; and stores the results in the storage unit 41 as acceleration information 411.

The candidate region extracting unit 401 divides the acceleration information 411 into multiple time-based sections. From among the multiple time-based sections, the candidate region extracting unit 401 extracts candidate regions from which feature values are to be calculated.

From the candidate regions extracted by the candidate region extracting unit 401, the candidate region selecting unit 402 selects an optimum region from which feature values are to be calculated.

The feature value calculating unit 403 calculates feature values for the region selected by the candidate region selecting unit 402.

The nodding determining unit 404 determines whether or not an action made by the user 3 is nodding by using a decision tree regarding the feature values calculated by the feature value calculating unit 403. Alternatively, the nodding determining unit 404 may make this determination by comparing the feature values with learned information 412, which results from determination results obtained in the past.

The determination result output unit 405 outputs a determination result 413 obtained by the nodding determining unit 404. Examples of the determination result 413 to be output include pieces of information regarding the number of times nodding is made, a duration of nodding, and a person who has performed nodding.

The storage unit 41 stores the action detection program 410 that causes the controller 40 to function as the acceleration information processing unit 400, the candidate region extracting unit 401, the candidate region selecting unit 402, the feature value calculating unit 403, the nodding determining unit 404, and the determination result output unit 405. The storage unit 41 also stores the acceleration information 411, the learned information 412, and the determination result 413.

The acceleration information 411 is information that is received from the sensor 1 and is stored in the storage unit 41 by the acceleration information processing unit 400.

The learned information 412 is constituted by determination results obtained by the nodding determining unit 404 in the past, and is used as a reference to be compared with the feature values calculated by the feature value calculating unit 403.

The determination result 413 is a determination result obtained by the nodding determining unit 404.

Operation of Action Detection Apparatus

Referring to FIGS. 3 to 11B, an operation performed by the action detection apparatus 4 will be described below.

Figure 3:
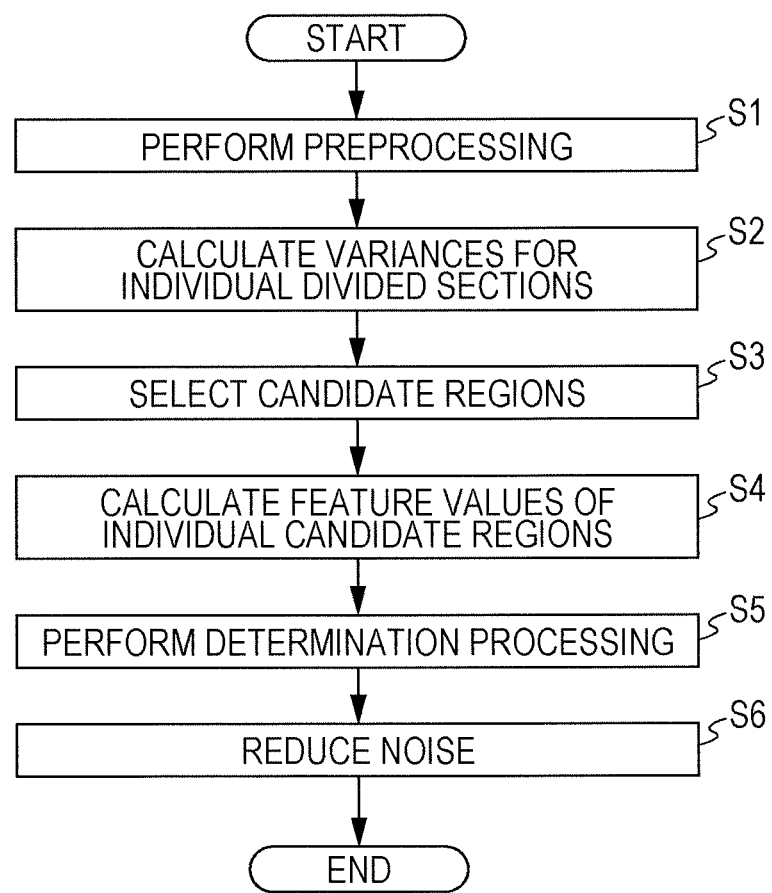
FIG. 3 is a flowchart illustrating an example operation performed by the action detection apparatus.

FIG. 3 is a flowchart illustrating an example operation performed by the action detection apparatus 4.

The acceleration information processing unit 400 first acquires, as acceleration information, accelerations detected by the sensor 1 in individual detection axis directions 100 to 102 of the sensor 1. The acceleration information processing unit 400 performs preprocessing, in which a gravitational acceleration component is subtracted from the acquired accelerations while assuming that the Y-axis direction of the sensor 1 is the vertical direction and in which the resulting values are stored as the acceleration information 411 (S1).

The candidate region extracting unit 401 then calculates a variance of acceleration in individual sections obtained by dividing the acceleration information 411 with respect to the time axis (S2). This is done because it is determined that some kind of action is made by the user 3 in a section with a large variance.

The user 3 may nod once such as "yes" or multiple times such as "yes, yes, yes". In order to detect both of these cases, an interval used in the division is set to, for example, one second.

The following describes an example of the acceleration information 411 and an example of a variance of acceleration.

Figure 4A:
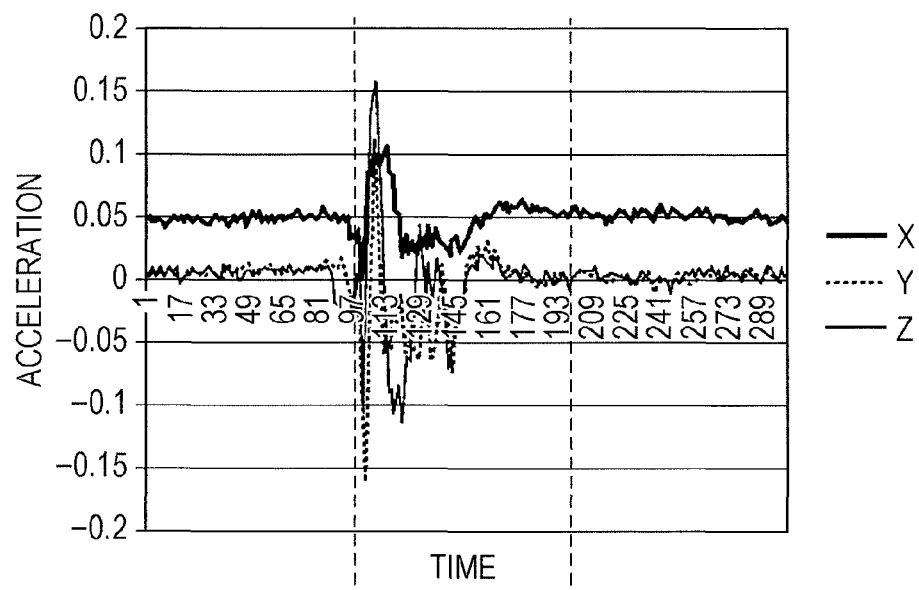
Figure 4B:
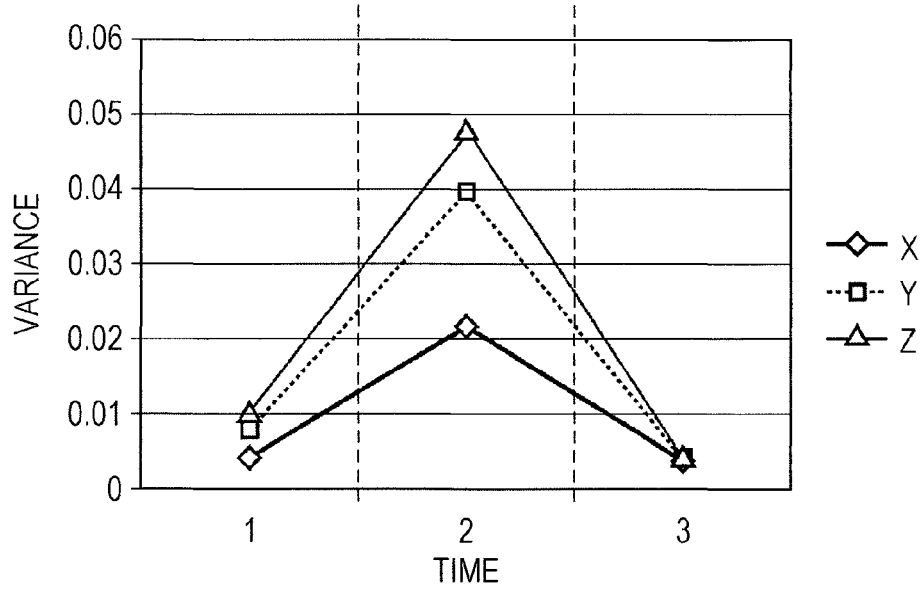
FIG. 4B is a graph illustrating an example of variances of the acceleration information in the individual axis directions.
Figure 5A:
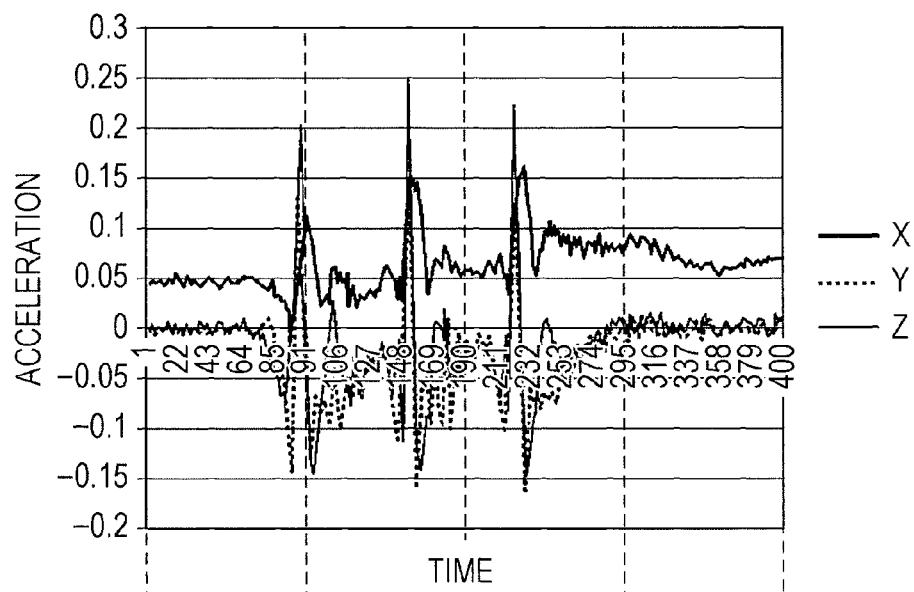

FIG. 4A is a graph illustrating an example of values of the acceleration information 411 in the individual axis directions, whereas FIG. 4B is a graph illustrating an example of variances of the acceleration information 411 in the individual axis directions. FIG. 5A is a graph illustrating another example of values of the acceleration information 411 in the individual axis directions, whereas FIG. 5B is a graph illustrating another example of variances of the acceleration information 411 in the individual axis directions.

For example, the acceleration information 411 is illustrated in manners as illustrated in FIGS. 4A and 5A in which the horizontal axis represents the time axis. The candidate region extracting unit 401 divides the acceleration information 411 by one second with respect to the time axis to obtain sections. The candidate region extracting unit 401 then calculates variances of accelerations in the individual sections, thereby obtaining pieces of information illustrated in FIGS. 4B and 5B.

Figure 5B:
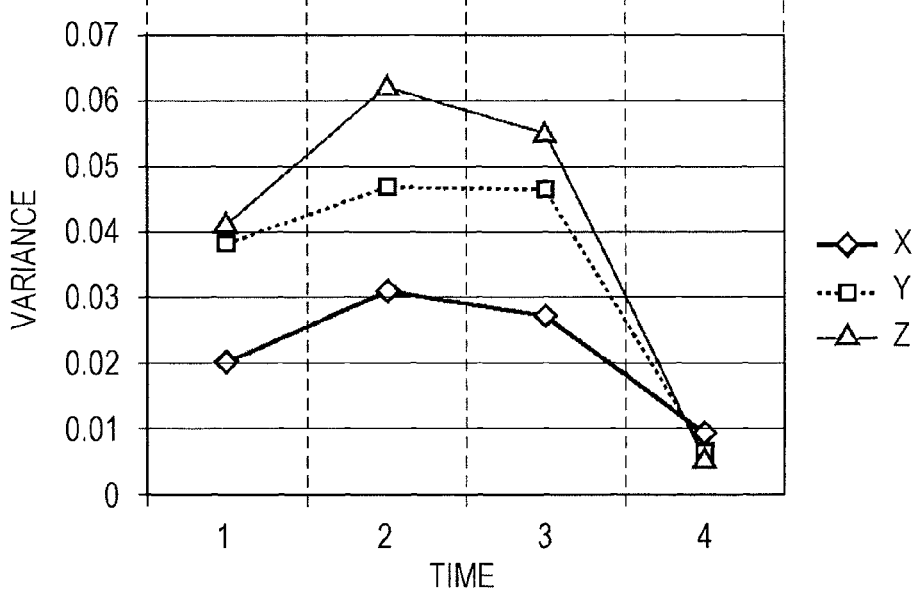
FIG. 5B is a graph illustrating another example of variances of the acceleration information in the individual axis directions.

The candidate region extracting unit 401 extracts, as a first candidate region, a section with the largest variance, for example, a second section in FIG. 4B or a second section in FIG. 5B. The candidate region selecting unit 402 shifts the first candidate region forward and backward by a predetermined time interval and selects the resultant sections as candidate regions (S3). An example method for shifting a section will be described below.

Figure 6A:
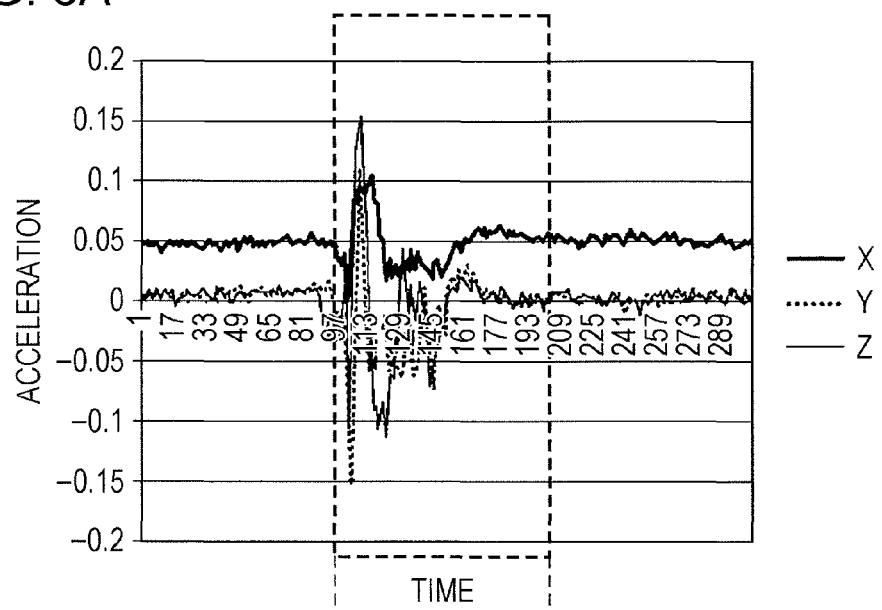
Figure 6B:
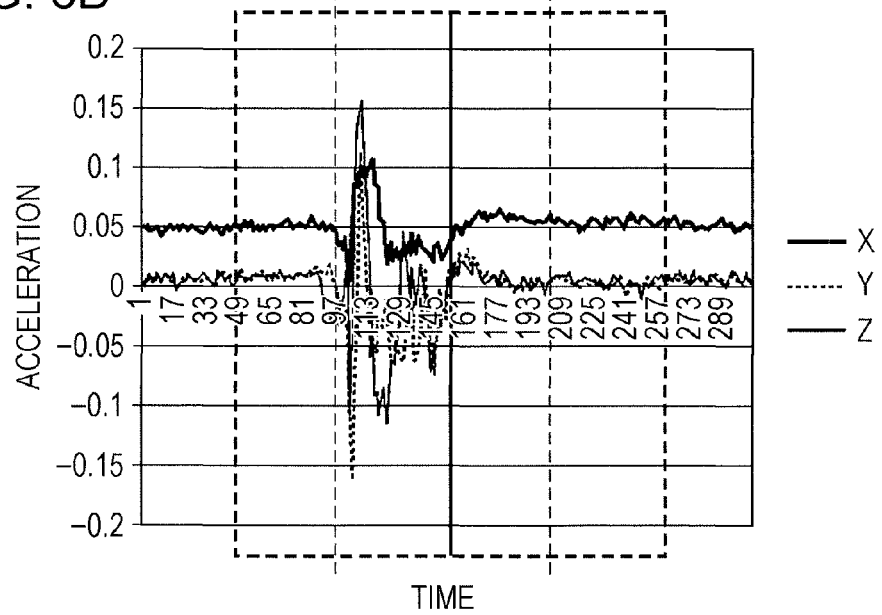
FIG. 6B is a graph illustrating an example of shifted candidate regions.
Figure 7A:
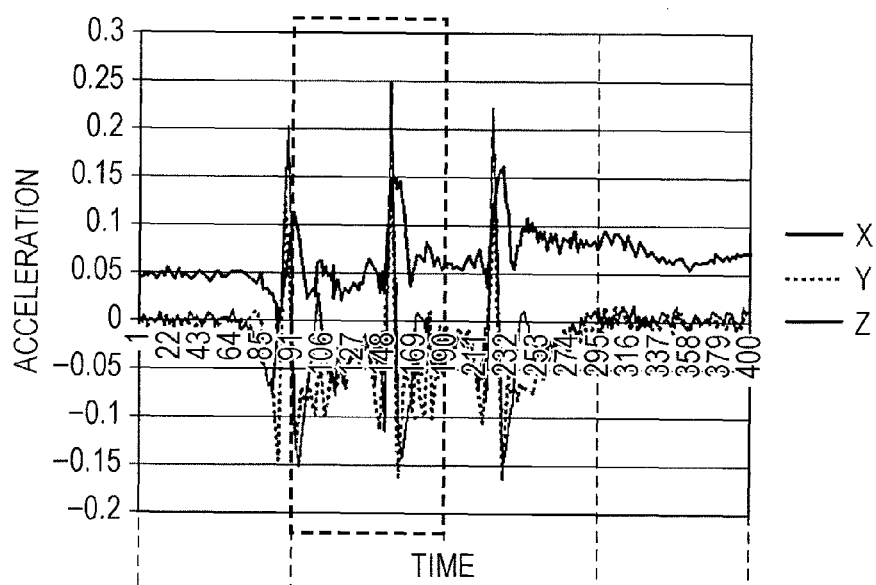
Figure 7B:
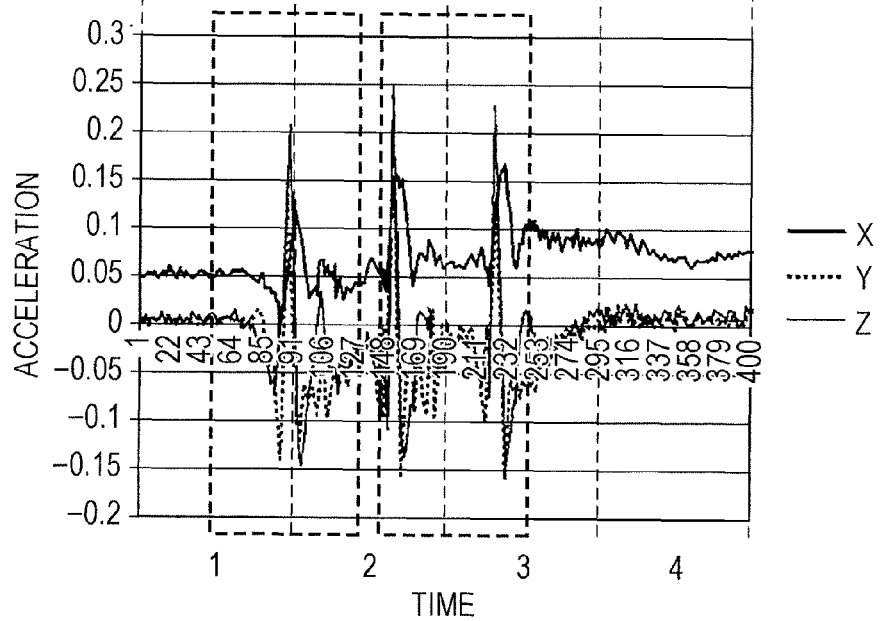
FIG. 7B is a graph illustrating another example of shifted candidate regions.

FIG. 6A is a graph illustrating an example of values of the acceleration information 411 in the individual axis directions and a candidate region, whereas FIG. 6B is a graph illustrating an example of shifted candidate regions. FIG. 7A is a graph illustrating another example of values of the acceleration information 411 in the individual axis directions and a candidate region, whereas FIG. 7B is a graph illustrating another example of shifted candidate regions.

Regarding the example illustrated in FIG. 6B, the candidate region selecting unit 402 selects, as candidate regions, sections that are obtained by shifting the second section illustrated in FIG. 6A forward and backward by 500 milliseconds. Also, regarding the example illustrated in FIG. 7B, the candidate region selecting unit 402 selects, as candidate regions, sections obtained by shifting the second section illustrated in FIG. 7A forward and backward by 500 milliseconds. Specifically, the candidate region selecting unit 402 selects, as a second candidate region, a section with the largest variance of acceleration from among the first candidate region, the section obtained by shifting the first candidate region forward, and the section obtained by shifting the first candidate region backward.

Subsequently, the feature value calculating unit 403 calculates feature values for the individual candidate regions selected by the candidate region selecting unit 402 (S4). In this exemplary embodiment, variances of accelerations in the individual axis directions are calculated as the feature values.

Based on the feature values calculated by the feature value calculating unit 403, the nodding determining unit 404 determines whether or not the action made by the user 3 is nodding (S5). Here, the determination is made using a decision tree described below.

Figure 9A:
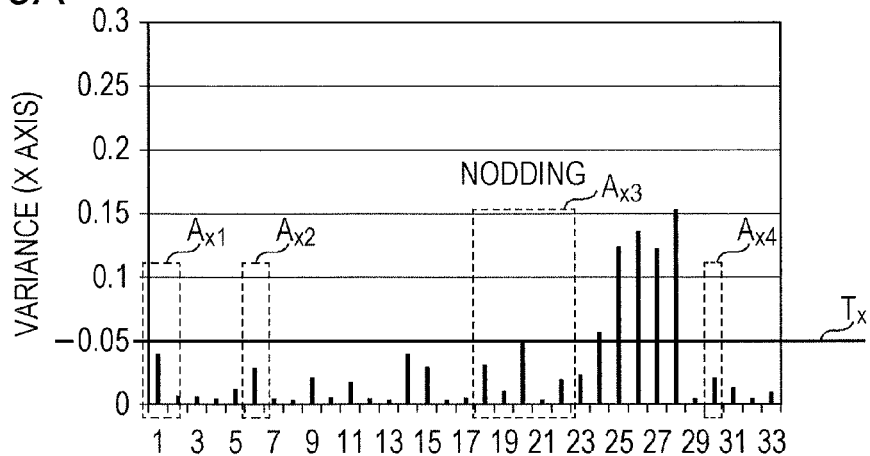
FIGS. 9A to 9C are graphs illustrating determination results obtained by the nodding determining unit from variances in the respective axis directions.
Figure 9B:
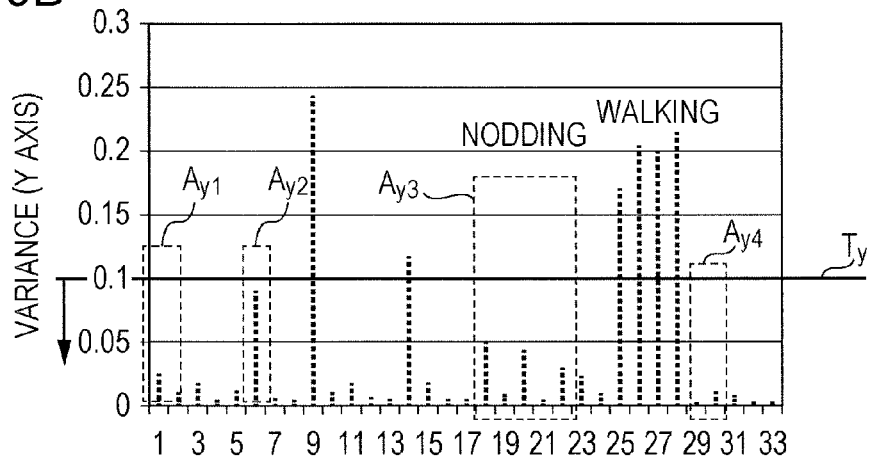
Figure 9C:
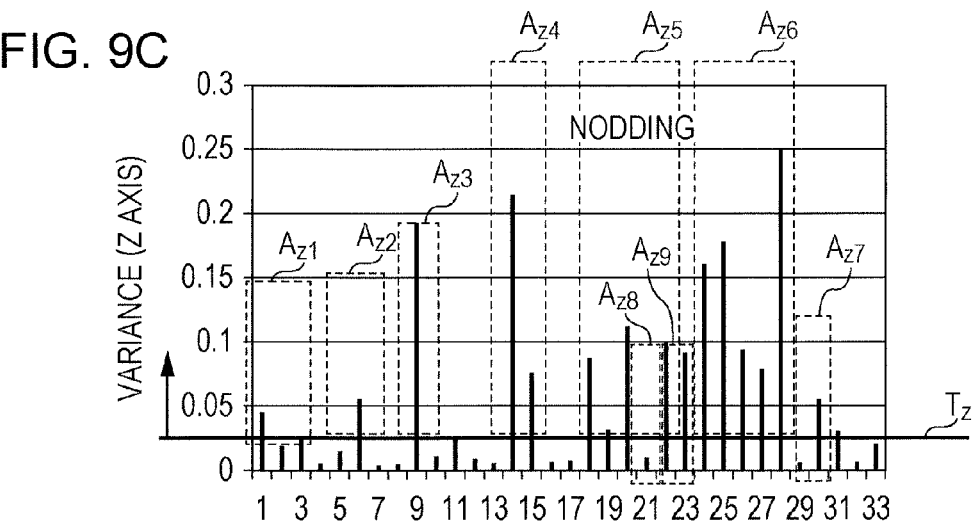

FIG. 8 is a flowchart illustrating an example operation performed by the nodding determining unit 404. FIGS. 9A to 9C are graphs illustrating determination results obtained by the nodding determining unit 404 based on variances in the individual axis directions.

If the Y-axis variance that is the feature value calculated by the feature value calculating unit 403 is 0.15 or greater (YES in S11), the nodding determining unit 404 determines that the action made by the user 3 is "walking" (S16). The curve of acceleration for "walking" resembles that for "nodding" but the variance of the vertical direction acceleration of the user 3 for "waking" is greater than that for "nodding". Thus, the action "walking" is excluded using this characteristic.

If the variance of the Z-axis acceleration is 0.02 or greater (YES in S12), the variance of the Y-axis acceleration is 0.10 or less (YES in S13), and the variance of the X-axis acceleration is 0.05 or less (YES in S14), the nodding determining unit 404 determines that the action made by the user 3 is "nodding" (S15). Here, the threshold of the variance of the Y-axis acceleration is set to 0.10 or less, for example. This value is decided based on experimental data or the learned information 412, and is set as an effective threshold for discriminating nodding from other actions. Also, the threshold of the variance of the X-axis acceleration is set to 0.05 or less, for example. This value is set based on experimental data or the learned information 412 in order to determine whether the lateral movement made by the user 3 relates to "nodding" or other actions.

FIGS. 9A to 9C illustrate determination results obtained with the above-described determination method. As illustrated in FIG. 9C, pieces of data that are equal to or greater than the threshold Tz=0.02 for the variance of the Z-axis acceleration are those contained in regions $A_{z1}$ to $A_{z9}$, which are obtained as determination results in step S12 illustrated in FIG. 8. Also, as illustrated in FIG. 9B, among the above-described pieces of data (the pieces of data contained in the regions $A_{z1}$ to $A_{z9}$) illustrated in FIG. 9C, pieces of data that are equal to or less than the threshold Ty=0.10 for the variance of the Y-axis acceleration are those contained in regions $A_{y1}$ to $A_{y4}$, which are obtained as determination results in step S13 illustrated in FIG. 8. Further, as illustrated in FIG. 9A, among the above-described pieces of data (the pieces of data contained in the regions $A_{y1}$ to $A_{y4}$) illustrated in FIG. 9B, pieces of data that are equal to or less than the threshold Tx=0.05 for the variance of the X-axis acceleration are those contained in regions $A_{x1}$ to $A_{x4}$, which are obtained as determination results in step S14 illustrated in FIG. 8.

The nodding determining unit 404 determines that the action made by the user 3 in these common regions (the regions $A_{x1}$ to $A_{x4}$ illustrated in the graph of the variance in the X-axis direction) is a "nodding" action. Verification made by the inventor indicates that the accuracy of this determination is 84.8%.

The following describes another verification result.

Figure 10A:
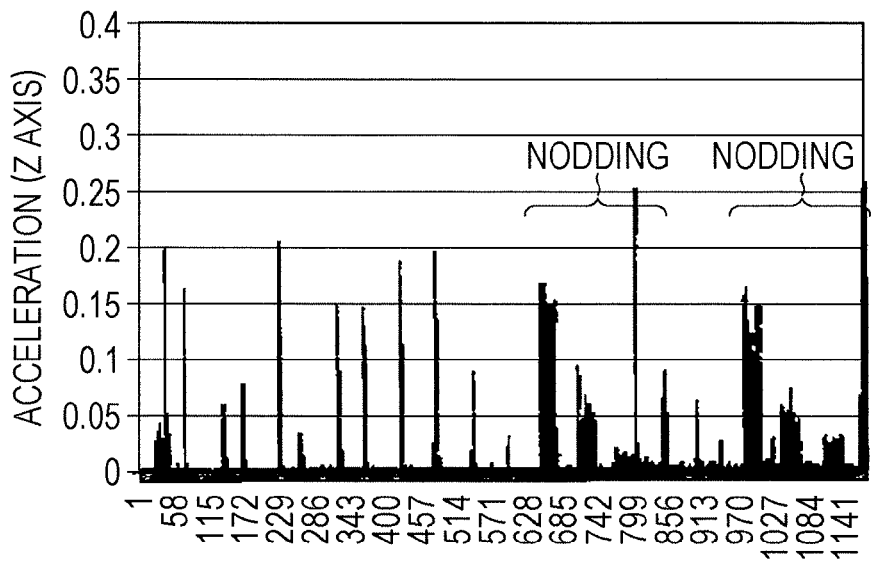
Figure 10B:
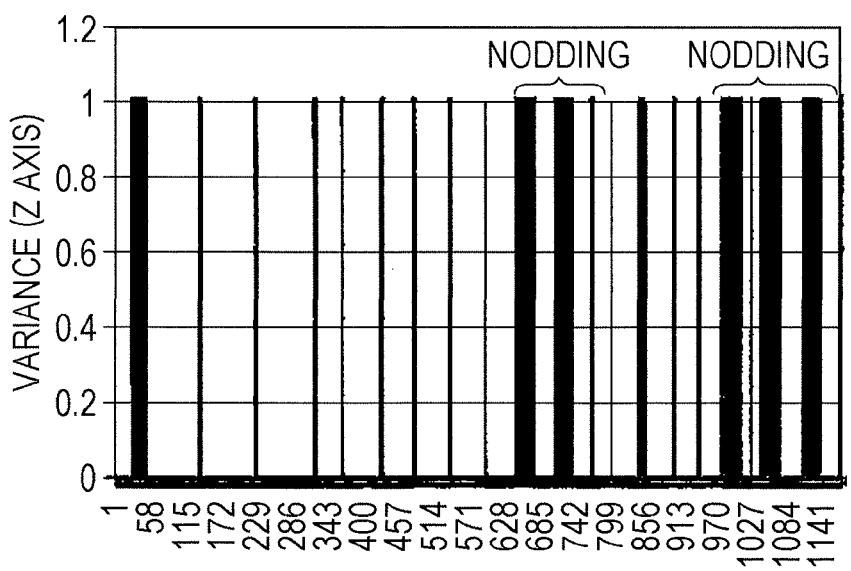
FIG. 10B is a graph illustrating a determination result obtained by the nodding determining unit from the variance in the Z axis direction.
Figure 11A:
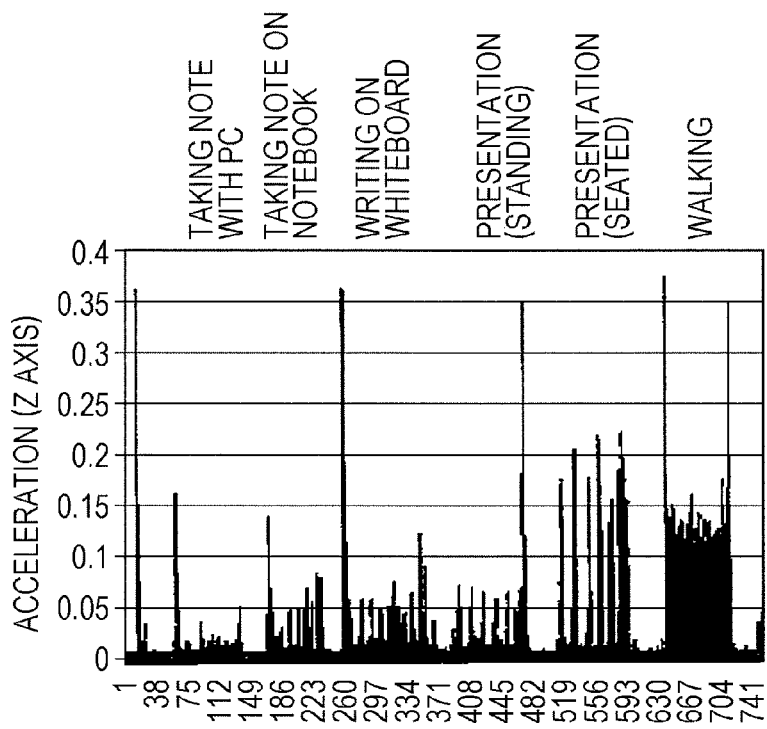

FIG. 10A is a graph illustrating an example of a value of the acceleration information 411 in the Z-axis direction, whereas FIG. 10B is a graph illustrating a determination result obtained by the nodding determining unit 404 from the variance in the Z-axis direction. FIG. 11A is a graph illustrating another example of a value of the acceleration information 411 in the Z-axis direction, whereas FIG. 11B is a graph illustrating a determination result obtained by the nodding determining unit 404 from the variance in the Z-axis direction.

Figure 11B:
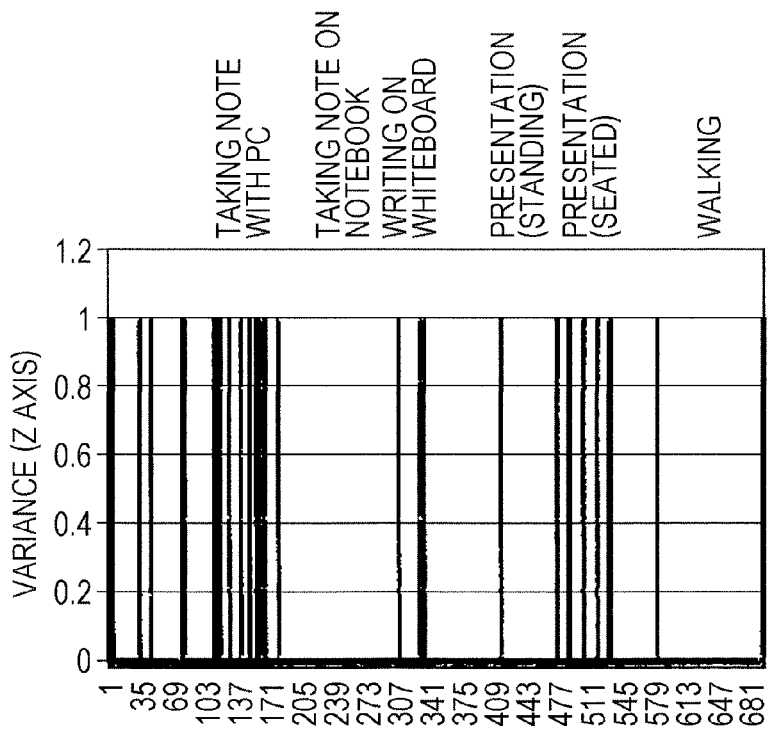
FIG. 11B is a graph illustrating a determination result obtained by the nodding determining unit from the variance in the Z axis direction.

FIGS. 10A and 10B illustrate a case where the actions made by the user 3 are "nodding", whereas FIGS. 11A and 11B illustrate a case where the actions made by the user 3 are not "nodding".

Compared with the determination result illustrated in FIG. 10B (in which the threshold for nodding is equal to one), the accuracy of pieces of data that are equal to or greater than the threshold Tz=0.02 in the variance of the Z-axis acceleration illustrated in FIG. 10A is 97.1%. Here, the nodding determining unit 404 determines data having a duration of 600 milliseconds or less as noise, thereby reducing noise (S6).

Compared with the determination result illustrated in FIG. 11B (in which the threshold for actions other than nodding is equal to one), the accuracy of pieces of data that are equal to or greater than the threshold Tz=0.02 in the variance of the Z-axis acceleration illustrated in FIG. 11A is 94.3%.

Other Exemplary Embodiments

The present invention is not limited to the above-described exemplary embodiment and various modifications may be made within the scope not departing from the gist of the present invention.

For example, the nodding determining unit 404 may use the Mahalanobis-Taguchi (MT) system based on reference feature values of nodding that are prepared in the learned information 412 to determine nodding. Alternatively, the nodding determining unit 404 may perform matching on a nodding curve of interest and a nodding curve prepared in the learned information 412 using dynamic time warping (DTW) to determine nodding.

Also, as described below, the candidate region extracting unit 401 may divide the acceleration information 411 by a time interval other than one second to obtain sections.

Figure 12A:
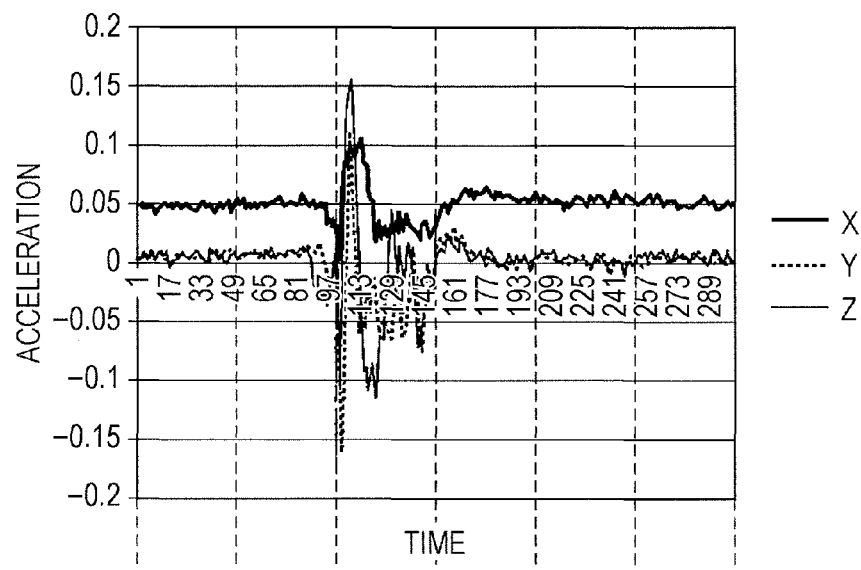
Figure 12B:
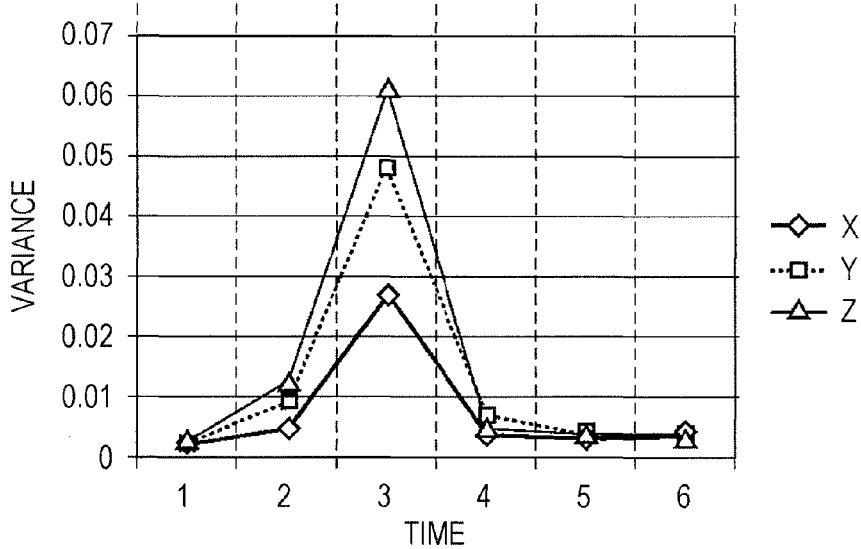
FIG. 12B is a graph illustrating an example of variances of the acceleration information in the individual axis directions.
Figure 13A:
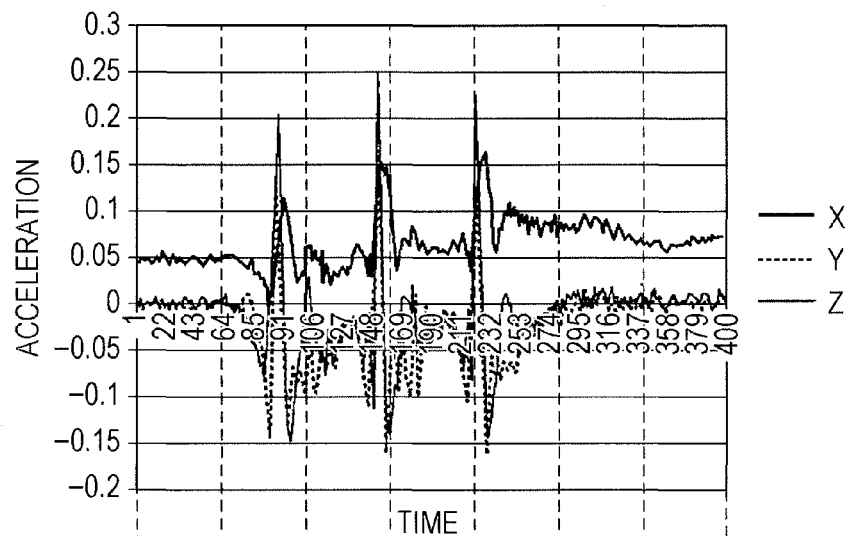

FIG. 12A is a graph illustrating an example of values of the acceleration information 411 in the individual axis directions, whereas FIG. 12B is a graph illustrating an example of variances of the acceleration information 411 in the individual axis directions. FIG. 13A is a graph illustrating another example of values of the acceleration information 411 in the individual axis directions, whereas FIG. 13B is a graph illustrating another example of variances of the acceleration information 411 in the individual axis directions.

For example, the acceleration information 411 is illustrated in manners as illustrated in FIGS. 12A and 13A in which the horizontal axis represents the time axis. The candidate region extracting unit 401 divides the acceleration information 411 by an interval of 600 milliseconds with respect to the time axis to obtain sections. The candidate region extracting unit 401 then calculates variances of accelerations in the individual sections, thereby obtaining pieces of information illustrated in FIGS. 12B and 13B.

Figure 13B:
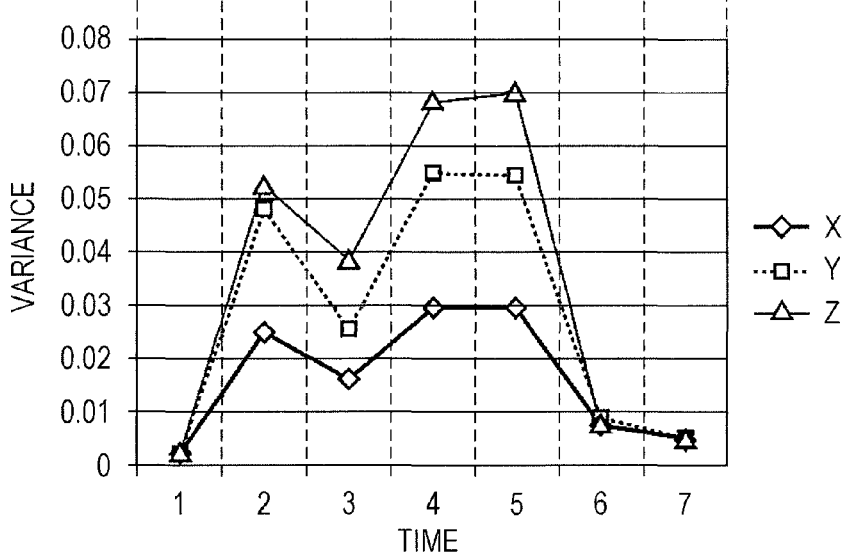
FIG. 13B is a graph illustrating another example of variances of the acceleration information in the individual axis directions.

The candidate region extracting unit 401 extracts, as the candidate region, a section with the largest variance, i.e., a third section in FIG. 12B or a fifth section in FIG. 13B. The candidate region selecting unit 402 shifts the candidate region forward and backward, and selects the resultant sections as new candidate regions (as in step S3).

Figure 14A:
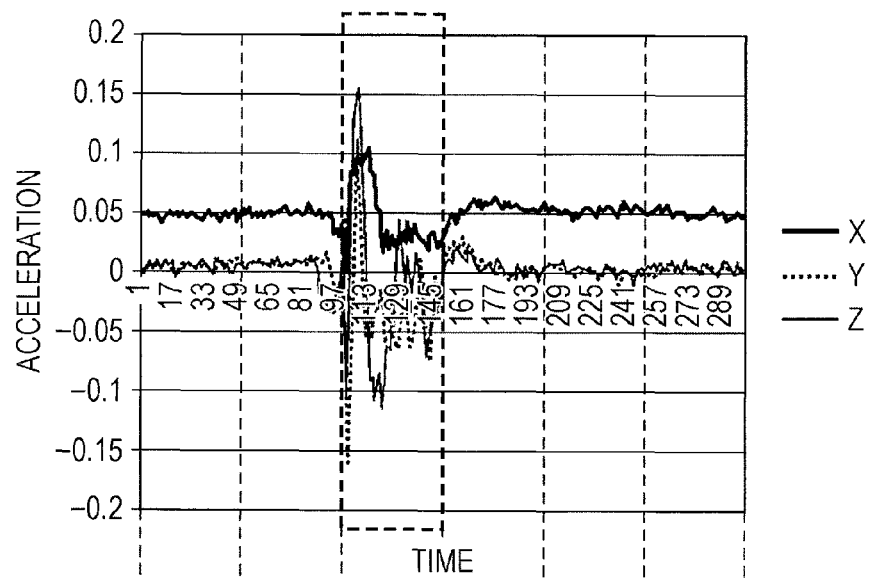
Figure 14B:
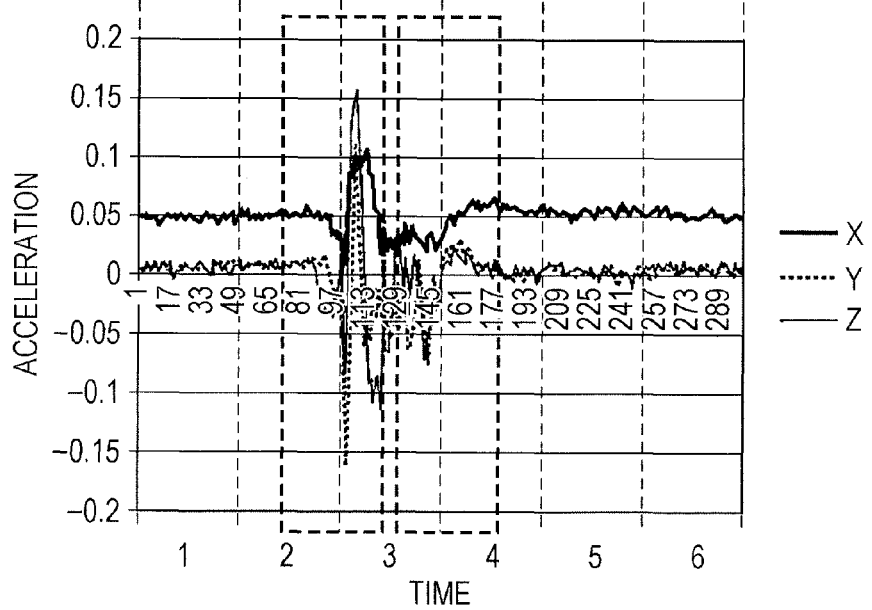
FIG. 14B is a graph illustrating an example of shifted candidate regions.
Figure 15A:
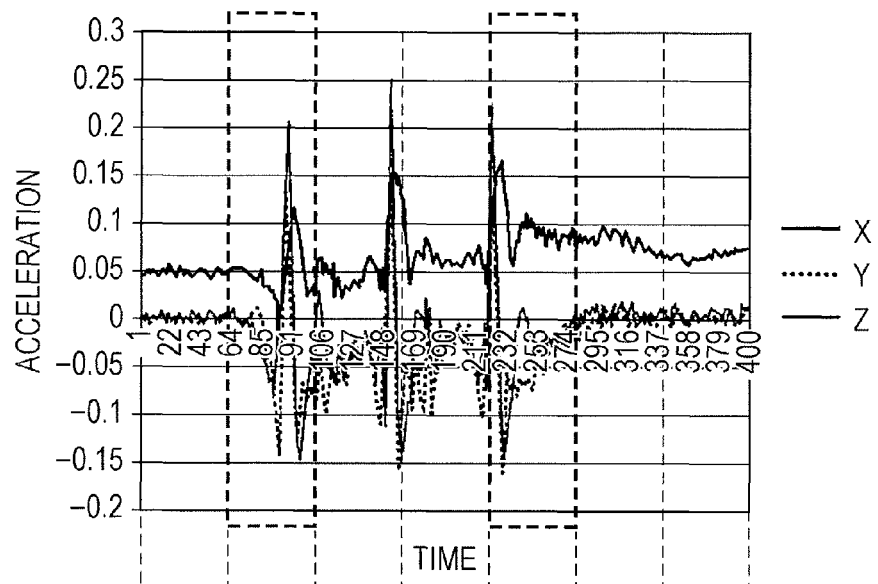
Figure 15B:
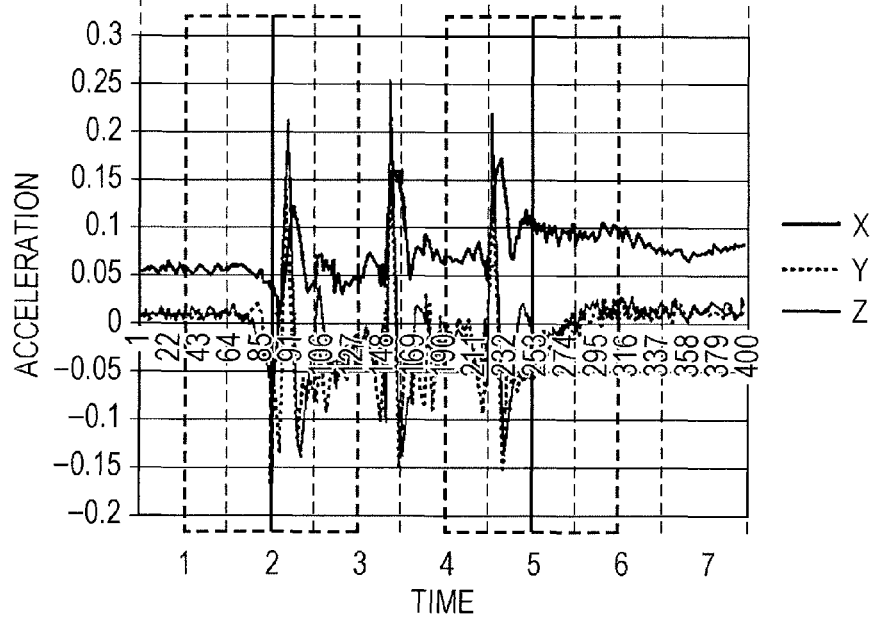
FIG. 15B is a graph illustrating another example of shifted candidate regions.

FIG. 14A is a graph illustrating an example of values of the acceleration information 411 in the individual axis directions and a candidate region, whereas FIG. 14B is a graph illustrating an example of shifted candidate regions. FIG. 15A is a graph illustrating another example of values of the acceleration information 411 in the individual axis directions and a candidate region, whereas FIG. 15B is a graph illustrating another example of shifted candidate regions.

Regarding the example illustrated in FIG. 14B, the candidate region selecting unit 402 selects, as candidate regions, sections obtained by shifting the third section illustrated in FIG. 14A forward and backward by 300 milliseconds. Also, regarding the example illustrated in FIG. 15B, the candidate region selecting unit 402 selects, as candidate regions, sections obtained by shifting the fifth section illustrated in FIG. 15A forward and backward by 300 milliseconds.

Subsequently, the feature value calculating unit 403 calculates feature values for the individual candidate regions selected by the candidate region selecting unit 402 (as in step S4). Here, variances of accelerations in the individual axis directions are calculated as the feature values.

As described above, by changing the time interval from one second to 600 milliseconds, a minimum section necessary for feature-value-based analysis may be obtained and the accuracy of determination may improve.

The above-described action detection program 410 may be provided after being stored on a storage medium, such as a compact disc-read only memory (CD-ROM), or may be downloaded to the storage unit 41 of the action detection apparatus 4 from a server apparatus connected thereto via a network, such as the Internet. Also, all or some of the acceleration information processing unit 400, the candidate region extracting unit 401, the candidate region selecting unit 402, the feature value calculating unit 403, the nodding determining unit 404, and the determination result output unit 405 may be implemented as hardware, such as an application specific integrated circuit (ASIC). The order of the steps of each operation described in the above exemplary embodiments may be changed, some of the steps may be omitted, or another step may be added to the steps.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A nodding action detection system comprising:
a sensor disposed on a lanyard configured for wearing on a neck of a user; and
a processor programmed to determine a nodding action of the user based on data transmitted from the sensor to a first communication unit of the processor, wherein
the sensor includes a second communication unit configured to transmit the data to the first communication unit of the processor, and
in response to the first communication unit receiving the data from the second communication unit of the sensor, the processor is programmed to:
calculate a variance of acceleration in first individual time sections obtained by dividing pieces of acceleration information for a plurality of axis directions by a first predetermined time interval, the pieces of acceleration information being included in the data transmitted by the second communication unit of the sensor to the first communication unit of the processor, the variance of acceleration being calculated for each of the plurality of axis directions;
extract, as a first candidate region, a time section with the largest variance of acceleration from among the first individual time sections;
calculate a variance of acceleration in second individual time sections obtained by shifting the first candidate region forward and backward by a second predetermined time interval which is shorter than the first predetermined time interval;
select, as a second candidate region, a time section with the largest variance of acceleration from among the first candidate region, the second individual time section obtained by shifting the first candidate region forward, and the second individual time section obtained by shifting the first candidate region backward;
calculate a feature value for the selected second candidate region;
determine the nodding action on the basis of the calculated feature value; and
output a determination result of the nodding action.

2. The nodding action detection system according to claim 1, wherein
the nodding action is determined using a decision tree regarding the calculated feature value.

3. The nodding action detection system according to claim 2, wherein
noise is determined using a component of the feature value corresponding to a forward direction of the user.

4. The nodding action detection system according to claim 1, wherein
the sensor is an acceleration sensor.

5. The nodding action detection system according to claim 2, wherein
the sensor is an acceleration sensor.

6. The nodding action detection system according to claim 3, wherein
the sensor is an acceleration sensor.

* * * * *